United States Patent [19]

Meier

[11] Patent Number: 5,248,570
[45] Date of Patent: Sep. 28, 1993

[54] STORAGE BATTERY

[75] Inventor: Hans A. Meier, Duderstadt, Fed. Rep. of Germany

[73] Assignee: Otto Bock Orthopaedische Industrie Besitz- und Verwaltungs-Kommanditgesellschaft, Duderstadt, Fed. Rep. of Germany

[21] Appl. No.: 789,673

[22] Filed: Nov. 8, 1991

[30] Foreign Application Priority Data

Nov. 22, 1990 [DE] Fed. Rep. of Germany ... 9015923[U]

[51] Int. Cl.⁵ .............................................. H01M 2/30
[52] U.S. Cl. .................................... 429/121; 429/97; 429/98; 429/123; 429/178
[58] Field of Search .................... 429/97, 98, 121, 123, 429/178

[56] References Cited

U.S. PATENT DOCUMENTS 4,399,201  8/1983  Nagahara .............................. 429/48

FOREIGN PATENT DOCUMENTS 2542933  3/1977  Fed. Rep. of Germany .

Primary Examiner—Prince Willis, Jr.
Assistant Examiner—M. Nuzzolillo
Attorney, Agent, or Firm—Foley & Lardner

[57] ABSTRACT

A storage battery having a housing with a plurality of contact forks which are opposite a switch disposed on the housing. The switch has a slider which slidably guides a portion of the switch inside the housing in a direction transverse to the housing longitudinal axis. A locking piece is resiliently fixed in the housing and holds the switch in place while allowing it to slide such that the switch is electrically connected and disconnected to the forks.

7 Claims, 1 Drawing Sheet

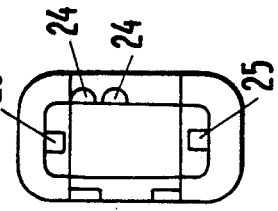
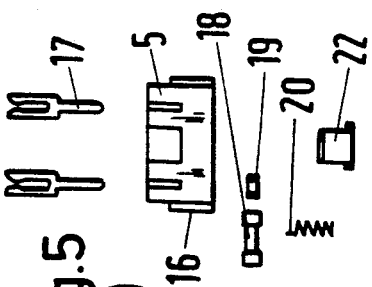
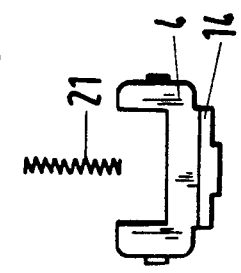
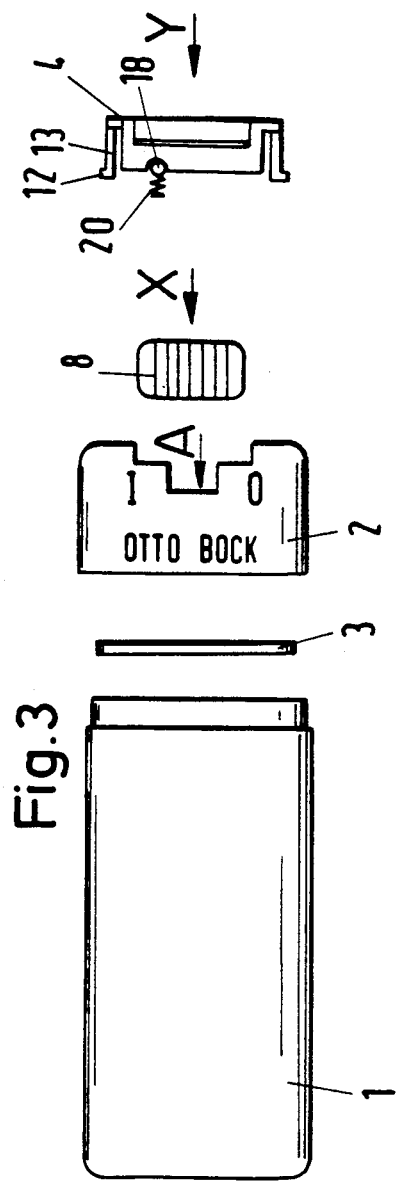
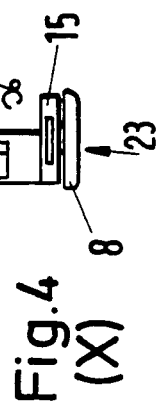
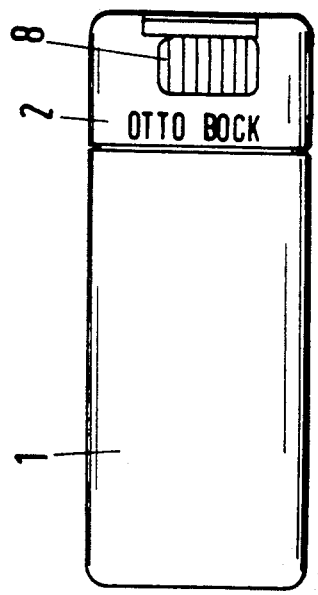
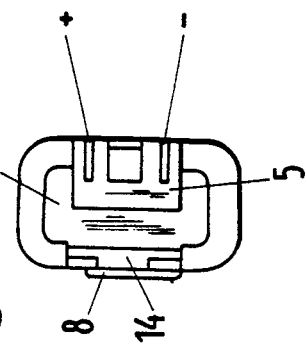

1

STORAGE BATTERY

BACKGROUND OF THE INVENTION

1. Field of the Invention

The invention relates to a storage battery for incorporation in a prosthesis which is externally powered by electricity, and more particularly to a storage battery provided with contact forks embedded in the front end thereof for engagement with knife-type contacts provided at the end of the prosthesis.

2. Description of the Related Art

A conventional storage battery can be found in German Patent Specification no. 2,542,933. Prostheses powered externally by electricity are controlled by myoelectric controls and electromechanical control systems, which are driven by a storage battery incorporated in the prosthesis. Previously known rechargeable storage batteries fit in a holder. These storage batteries can be integrated in all types of shafts, and because of their small external dimensions, can also be inserted into the case of long stumps. Provided in the prothesis are knife-type contacts which, upon insertion of the storage battery into the holder, engage with the contact forks of the storage battery. A snap-type closure is provided for securing the storage battery in its holder.

A switch for the electrical supply is provided outside the storage battery, and its holder, and is integrated, for example, in a hand prosthesis and is activated from the outside through the hand covering.

SUMMARY OF THE INVENTION

An object of the invention is to simplify the previously known storage battery with respect to its handling.

According to the invention, this object is achieved by arranging a sliding switch on the large face of the battery housing which lies opposite to the contact forks. The sliding switch is guided, within the housing and transverse to the longitudinal axis of the housing, by means of a slider which is equipped with contact springs, and is fixed in its sliding plane by means of a locking piece resiliently snapped into the housing.

According to the invention, a detachable connecting part, equipped with contact forks, can be detachable connected into the locking piece. The connecting part has a safety arrangement inserted therein which is in electrical communication with a contact fork.

Thus, according to the invention, the switch is integrated directly into the storage battery. However, the construction according to the invention affords the possibility of reducing the external dimensions of the storage battery as compared to conventional designs. Additionally, the housing of the conventional storage battery consists of a top part and a bottom part, each part being designed in the form of a flat shell. According to the invention, it is advantageous for the sliding switch, locking piece and connecting part to be accommodated in a housing head, which is glued to the housing body. The switch can be connected as a main switch allowing the entire current supply to be switched centrally switched on and off. The storage battery is particularly suitable for incorporation in a hand prosthesis for children, in which case a person attending to the disabled child has easy access to the switch.

BRIEF DESCRIPTION OF THE DRAWINGS

Other objects, features, and advantages of the present invention will become apparent from the following detailed description and accompanying drawings wherein:

FIG. 1, is a plan view of a storage battery;

FIG. 2, is a right side elevational view of the storage battery of FIG. 1;

FIG. 3, is an exploded plan view of the storage battery of FIG. 1;

FIG. 3a is a right side elevational view of FIG. 3 as viewed along arrow A;

FIG. 4, is an exploded view of a sliding switch; as viewed along arrow X of FIG. 3; and FIG. 5, is an exploded view of a locking piece with a connecting part as viewed along arrow Y of FIG. 3.

The storage battery shown comprises a housing, which is made up of a housing body 1 and a housing head 2 which are glued together. A distancing pad 3 and a storage battery unit (not shown) are pushed into the housing body 1. The housing head 2 encloses a sliding switch 23, a locking piece 4 and a connecting part 5, the design of which will be described hereinbelow.

The sliding switch 23 consists of a slider 6 which is guidably displaceable in the housing head 2 in a direction transverse to the longitudinal axis of the housing; is equipped with a contact spring 7, and bears on a slide button 8, which lies on a large face of the housing body 2. The slider 6 bears, via a resilient arm 9, on a guide (not shown) inside the housing head 2, and engages via a locking nose 10, situated at the end of the arm 9, notches 24 which fix fixing the switching position of the sliding switch. The contact spring 7 is held in place by a pin 11.

The slider 6 is fixed in its sliding plane inside the housing head 2 by the locking piece 4 which is pushed into the housing 2 and fixed resiliently therein. In its pushed-in position, the locking piece 4 lies flush with the end face of the housing head 2. The locking piece 4 has two spring tongues 13 lying opposite each other which are each equipped with a locking nose 12. Spring tongues 13 couple the locking piece 4 to the housing head 2 by engaging the locking noses 12 behind correspondingly designed undercuts 25 in the housing head 2. In an end view of the housing head 2, the locking piece 4 has a U-shape and engages with a frame 14 over a branch 15 of the slider 6.

The connecting part 5 fits between the U-branches of the locking piece 4. Lateral guide noses 16 thereby engage with corresponding guide grooves (not shown) on the inner side of the U-branches. The connecting part 5 is equipped, on its side facing away from the slide button 8, with contact forks 17. One of the forks 17 is electrically connected to a safety arrangement (such as a fuse) 18. The safety arrangement 18 fits into the connecting part 5 in a direction parallel to the U-branch of the locking piece 4, and is held clamped in place by a bracket 19 at one end and engages with its free end a corresponding recess in the locking piece 4 when the connecting part 5 is pushed fully in place. A compression spring 20 bears against the safety arrangement 18 at a right angle. In its assembled position, the connecting part 5 engages, with the free ends of its guide noses 16 facing toward the contact forks 17, behind a shoulder (not shown) of the housing head 2. The connecting part 5 must therefore be pushed fully into the locking piece 4 before the locking piece 4 is in turn pushed into the end opening of the housing head 2. The connecting part 5 is electrically connected and disconnected from the contact spring 7 depending on whether or not the contact spring 7 is in contact with the safety arrangement 18 as the contact spring 7 moves with the switch 23. Additionally, a second contact spring (not shown) moves with the switch 23 into and out of electrical contact with the contact fork 17 which is not connected to the safety arrangement 18.

Arranged between the contact forks 17 is a pressure part 22 which can be displaced upward due to the action of a spring 21. Thus, when the storage battery is fit into an adapted holder inside a prosthesis, the pressure part 22 is pressed in by a prosthesis-side nose to lock the storage battery in place. When the storage battery is unlocked, the pressure part 22 presses the storage battery up and out of the holder on one side so as to facilitate the removal of the storage battery. Further details on this feature can be found in German Patent Specification 2,542,933 the subject matter of which is hereby incorporated by reference.

While specific embodiments of the invention have been described, it will be understood that the invention is capable of modification and this application is intended to cover any variations, use or adaptation of the invention and including such departures from the present disclosure as to come within the knowledge of customary practice in the art to which the invention pertains, and as may be applied to the essential features hereinbefore set forth and following within the scope of the invention and the limits of the appended claims.

What is claimed is:

1. A storage battery, comprising:
   a housing having opposing first and second sides and a longitudinal axis;
   a plurality of contact forks disposed near said first side;
   a switch, slidably disposed on said second side, having a slider which slidably guides a portion of said switch inside of said housing in a direction transverse to said longitudinal axis, said switch being electrically connected and disconnected to said forks during the movement of said switch in said transverse direction; and
   a locking piece resiliently fixed in said housing, said locking piece holding said switch in a fixed sliding plane.

2. A storage battery according to claim 1, further comprising a connecting part detachably connected within said locking piece, and a safety arrangement mounted in said connecting part, wherein said forks are connected to said connecting part and one of said forks is connected to said safety arrangement.

3. A storage battery according to claim 1, wherein said slider has a resilient arm and said housing has a guide disposed therein, said resilient arm bearing against said guide and having a locking nose at an end thereof which engages a notch in said housing thereby fixing a switching position of said switch.

4. A storage battery according to claim 1, wherein said locking piece has a pair of opposed spring tongues, each of said spring tongues having a locking nose thereon and being disposed in said housing such that said locking piece is resiliently fixed against an end of said housing.

5. A storage battery according to claim 2, wherein said connecting part is detachably connected to said locking piece in a direction traverse to said housing longitudinal axis.

6. A storage battery according to claim 2, wherein said housing includes a housing head and a housing body which are glued together, and said locking piece and said connecting part are disposed in said housing head.

7. A storage battery, comprising:
   a housing having opposing first and second sides and a longitudinal axis;
   a plurality of contact forks disposed near said first side;
   a switch, slidably disposed on said second side, having a slider which slidably guides a portion of said switch inside of said housing in a direction transverse to said longitudinal axis, said switch being electrically connected and disconnected to said forks during the movement of said switch in said transverse direction;
   a locking piece resiliently fixed in said housing, said locking piece holding said switch in a fixed sliding plane;
   a connecting part detachably connected within said locking piece; and
   a safety arrangement mounted in said connecting part, wherein said forks are connected to said connecting part and one of said forks is connected to said safety arrangement; and
   wherein said slider has a resilient arm and said housing has a guide disposed therein, said resilient arm bearing against said guide and having a locking nose at an end thereof which engages a notch in said housing thereby fixing a switching position of said switch.

* * * * *